United States Patent [19]

Lemke

[11] Patent Number: 4,498,481
[45] Date of Patent: Feb. 12, 1985

[54] ESTRUS CYCLE MONITORING SYSTEM
[76] Inventor: Judith K. Lemke, 4263 170th St. E., Rosemount, Minn. 55068
[21] Appl. No.: 425,893
[22] Filed: Sep. 28, 1982
[51] Int. Cl.³ .............................................. A61B 5/05
[52] U.S. Cl. ................................. 128/734; 128/736
[58] Field of Search .................. 128/736, 738, 303.1, 128/6, 734, 639, 642, 670, 788, 789, 784

[56] References Cited
U.S. PATENT DOCUMENTS

| | | | |
|---|---|---|---|
| 4,148,304 | 4/1979 | Mull | 128/738 |
| 4,224,949 | 8/1980 | Scott et al. | 128/734 |
| 4,274,419 | 6/1981 | Tam et al. | 128/784 |
| 4,343,300 | 8/1982 | Hattori | 128/6 |

Primary Examiner—Kyle L. Howell
Assistant Examiner—Deidre A. Foley
Attorney, Agent, or Firm—Hugh D. Jaeger

[57] ABSTRACT

Estrus cycle monitoring (ECM) system for detecting estrus in female mammals and human females by measuring electrical resistance of mucus in the vaginal cavity. A hand-held electrical package including readout for temperature as well as conductivity of the mucus includes a longitudinal probe supported by a stainless steel elongated rod positioning in the vagina, the probe also including an objective lens with a diffuser lens for observing vaginal interior and cervix color, size, and dilation through a fiber-optic bundle running the length of the elongated rod, and an eye-imaging optic connected at the other end of the fiber-optic bundle for observing the same. The electronic housing includes an LCD display, a temperature-conductivity switch, a light switch, and an on/off switch. The probe includes two gold-plated twin-helix electrodes supported in molded plastic about the circumference of the probe, and the objective lens with the diffuser lens surrounding the same for transmitting light for veiwing of the vagina and cervix. The utilization of a fiber-optic scope, electrical resistance reading of the mucus, and temperature of the vagina provide for determining the stage of estrus, which is particularly designed for insemination of horses, cattle, hogs, sheep, or human females as determined by the size of the probe and the length of the rod.

8 Claims, 7 Drawing Figures

Electric resistance of the vaginal mucus in a cow, recorded and telemetrically transmitted from a probe permanently attached to the external os of the cervix.

ESTRUS CYCLE MONITORING SYSTEM

BACKGROUND OF THE INVENTION

1. Field of the Invention

The present invention pertains to an estrus cycle monitoring (ECM) system and, more particularly, pertains to an ECM apparatus including a fiber-optic scope, electrical resistance reading of mucus, and thermometer for determining the temperature of the vaginal cavity.

2. Description of the Prior Art

The prior art measuring devices for determining the electrical resistance or conductivity of mucus have suffered numerous electrical as well as mechanical difficulties. The prior art devices have not been sealed to the environment and therefore have been subject to humidity, moisture, and foreign objects in the devices, such as animal hairs, animal feces, and just plain old barnyard dirt. These have caused erratic readings, and also the readings have not been consistent over time.

Another problem with the prior art devices has been the type of electrode configuration or the coatings over the electrodes which have not always provided for consistent readings over a period of time. The electrodes also would not provide accurate reading in such animals as cattle, horses, sheeps, or hogs. It is important to inseminate the animals at the correct time so as not to lose time in breeding as well as losing money in the inseminating sperm obtained from breeding co-ops or collecting co-ops or like organizations.

Finally, the prior art devices have not provided for viewing of the vaginal cavity of the cervical os, or taking the temperature of the vaginal cavity.

The present invention overcomes the disadvantages of the prior art by providing an ECM system which provides for accurate electrical resistance reading of the mucus, provides a fiber-optic scope for viewing of the cervix and the vaginal cavity, and provides a thermometer for taking the vaginal cavity temperature all in a hand-held probe device including an electronics package with a nicad battery which is sealed to the environmental elements.

SUMMARY OF THE INVENTION

The general purpose of the present invention is to provide an estrus cycle monitoring system including an electronics package sealed to the elements of the environment and including an LCD readout for conductivity of mucus as well as vaginal temperature. A rod supports on one end an elongated probe including helix electrodes, an objective and diffuser lens, and on the other end an eye-imaging optic for visual viewing of the cervix color, size and dilation through the fiber-optic scope. The pistol-grip type probe and handle provides for convenient usage by any individual in an agricultural environment, or in a medical or surgical environment when the instrument has been sized and designated for use with a human female. The combination of the resistance monitoring, the speculum, and the thermometer provides for a specific part of an overall total diagnosis. The unit is self-contained and easily held and utilized by the individual in the appropriate environment. While the system is specifically designed to monitor the estrus of a mammal, the system also can detect abnormalities such as infections, follicular cysts, active luteal function, as well as other types of diseases.

According to one embodiment of the present invention, there is provided an estrus cycle monitoring system including a pistol-grip handle supporting an electronics housing, an elongated rod extending outwardly from one end thereof, a probe on the end of the rod supporting two gold- or platinum-plated helix electrodes supported in molded plastic, a temperature sensor on one side thereof, an objective lens surrounded by a diffusing lens, the objective lens connected to a coherent fiber-optic bundle extending along the length of the rod, through the electronics package, out the other end of the electronics package to an eye-imaging optic on an optic bundle, a random fiber-optic bundle connected to the diffuser lens, down the length of the elongated rod to a light source lamp in the electronics housing, electronic circuitry including an LCD display, decoder and buffer drivers, an A/D converter, the sample and hold and timer, and an AC signal generator connected in series through a temperature sensor, the spiral electrode helix assembly, and a switch for switching between temperature or conductivity readings on the LCD display whereby the instrument provides for reading of the electrical resistance and conductivity of the cervical mucus, provides for viewing of the vaginal cavity and cervix, and provides for measuring the temperature of the vaginal cavity status as well as detecting for abnormalities. The probe goes into the vagina and measures electrical resistance of mucus from the uterus and cervix. The switches as well as the readout can be positioned above the handle on the rear of the electronic housing for thumb actuation. The rod can be of stainless steel, while the probe is plastic or the like.

One significant aspect and feature of the present invention is an estrus cycle monitoring system providing for diagnosis of mucus by detecting electrical resistance, detecting the temperature in the vaginal cavity, and visual viewing of the vaginal cavity through a fiber-optic scope. A helix designed electrode of the probe allows for consistent electrode contact with the mucus. The temperature reading of the vaginal cavity is particularly important and inherently is provided by the temperature sensor in the plastic capsulated probe.

Another significant aspect and feature of the present invention is an electronics package which is completely sealed, eliminating oxidation to the batteries or contamination by dirt, dust, hair or moisture within the electronics package itself, especially when used in an agricultural environment. The unit is self contained with the exception of a battery pack worn on an individual's belt and connected to the electronics package by a flexible cable.

A further significant aspect and feature of the present invention is a readout unit in the handle, providing a hands-on situation and for maneuvering, especially around the tail of an animal. While making these measurements, the tail of the animal sometimes gets in the way especially around the vulvular area requiring that one hand operates the unit while the other hand can appropriately maneuver the tail, etc.

An additional significant aspect and feature of the present invention is a probe which can be varied according to the size of the animal or the human female on which it is utilized.

Having thus described the invention, it is the principal object hereof to provide an estrus cycle monitoring system.

One object of the present invention is to provide an estrus monitoring system which combines the use of three known indicators of estrus—temperature, electrical resistance of mucus, and visual viewing of the vaginal cavity. Visual viewing includes the vagina, the cervix, and all anatomy of the reproductive tract and the physiology thereof. This physiology and anatomy relates both to humans and other mammals.

Another object of the present invention is an ECM system which is particularly useful in the agricultural field, specifically in the barnyard or in the barn. The device is protected from the elements, can easily be held in one hand, and easily utilized by one individual.

A further object of the present invention is to provide an ECM system which aids in expediting the pregnancy of either an animal or a human, more particularly intended for use with animals but also certainly utilizable with humans. This leads to greater profit and income from the animal in not only providing young, but also leads to a saving in the cost of sperm in artificial insemination practices. Profit is maximized by proper timing of artificial insemination, which is at the low-resistance point of the mucus. This period of time is the appropriate time to breed, between the standing heat time and the out-of-heat time. The best time to breed of course is from the middle of standing heat to about six hours after the end of heat.

A further object of the present invention is an ECM system which not only provides for electrical resistance readings of the mucus, but also provides for determination of abnormality, such as pneumovagina, luteal function, no ovulation or follicle, infections or urine pooling, severe infection as pyometria. The device is not only a diagnostic tool for determining the best possible time for insemination, but is also a diagnostic tool for determining potential reproductive abnormalities.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
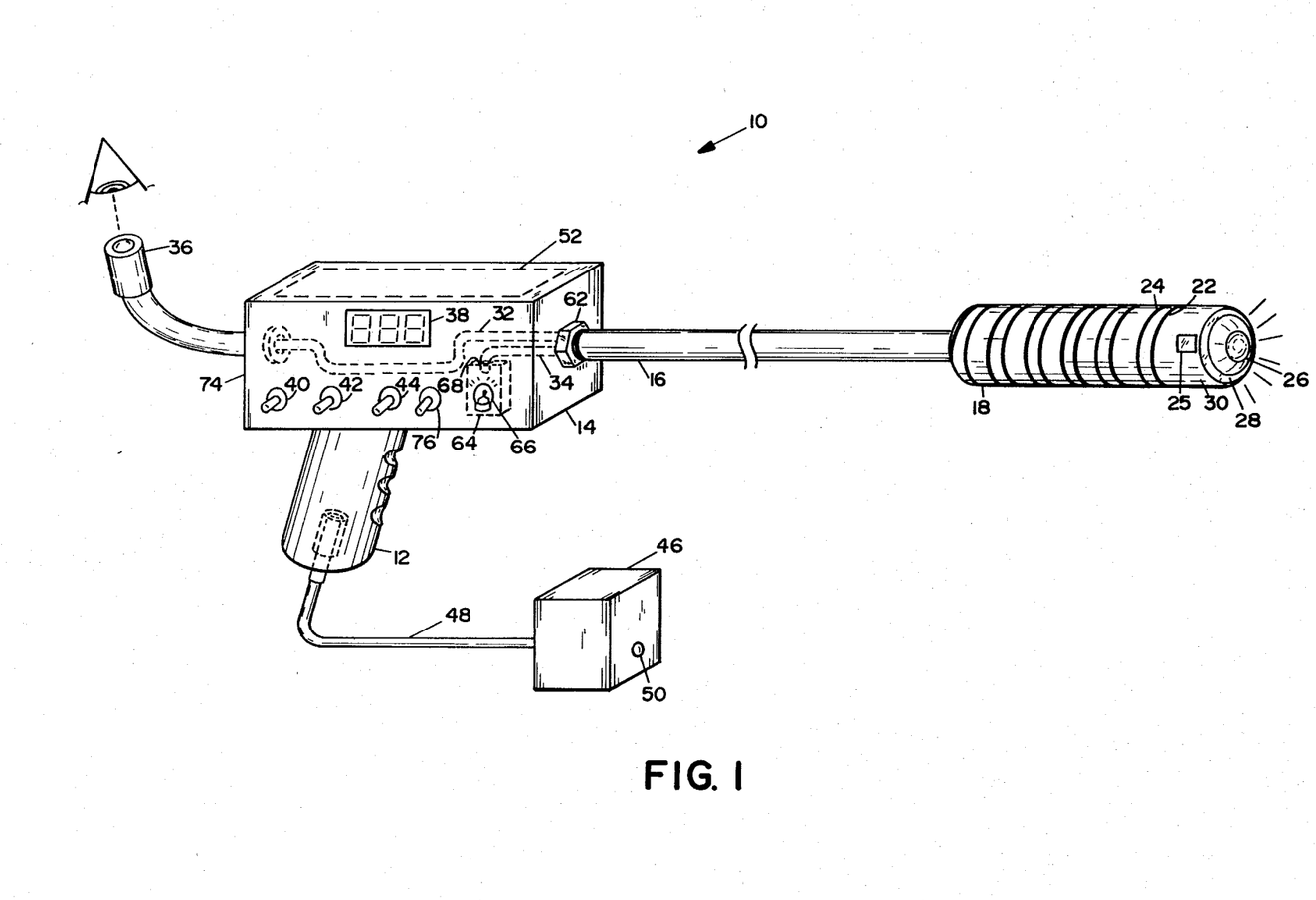
FIG. 1 illustrates a plan view of an estrus cycle monitoring system, the present invention.

FIG. 1 illustrates a plan view of an estrus cycle monitoring system 10 including a pistol-grip handle 12, an electronics housing 14 secured to the handle, an elongated rod 16 supporting a probe 18 at an end and secured to the electronics housing 14. Twin helix electrodes 22 and 24 connected together being either platinum- or gold-plated stainless springs secured in a molded plastic housing as later described in FIG. 2. A temperature sensor 25, an objective lens 26 surrounded by a diffuser lens 28 in the molded plastic 30 connects to a coherent fiber-optic bundle 32 and a random fiber-optic bundle 34. The coherent fiber-optic bundle 32 extends from the objective lens 26, through the rod 16, through the electronics housing 14, back through the end of the housing to an eye-imaging optic 36. An LCD display 38 can position on either the side of the housing or on the back of the housing as convenient. Switches below the LCD display 38 include a read switch 40, a temperature-electric resistance switch 42, and a light switch 44. A rechargeable battery connects to the electronics housing circuitry. The rechargeable battery 46 can be a nicad battery or the like which can be plugged into a suitable transformer plug with a flexible cable 48 plugging into a recharging plug 50 on the battery pack 46. An on/off switch 76 connects in the power circuit.

Figure 2:
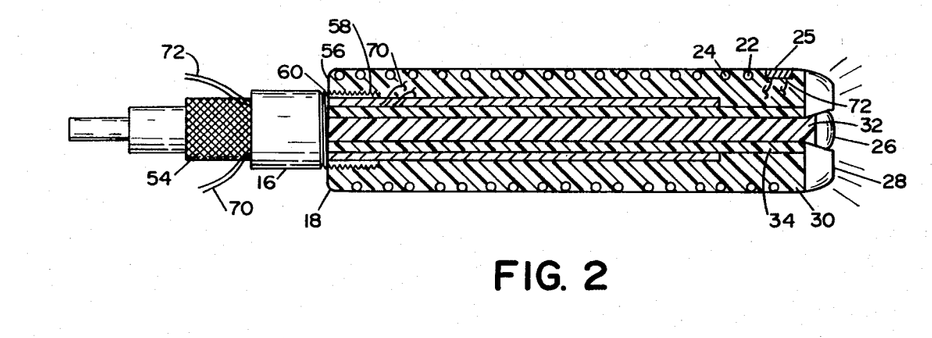
FIG. 2 illustrates a sectional view of a probe.

FIG. 2 illustrates a cross-sectional view of the rod 16 and probe 18 assembly where numerals correspond to those elements previously described. Wires connect the electrodes to the electrical circuit board 52 of FIG. 3 as later described in detail, and a covering 54 extends over the random fiber bundle 34. The molded plastic end 56 of the probe 18 can include threads 58 to screw over threads 60 of the end of the rod 16. The rod can secure to the electronics housing with nuts and bolts 62 or any other suitable mechanical adaptation thereof.

Figure 3:
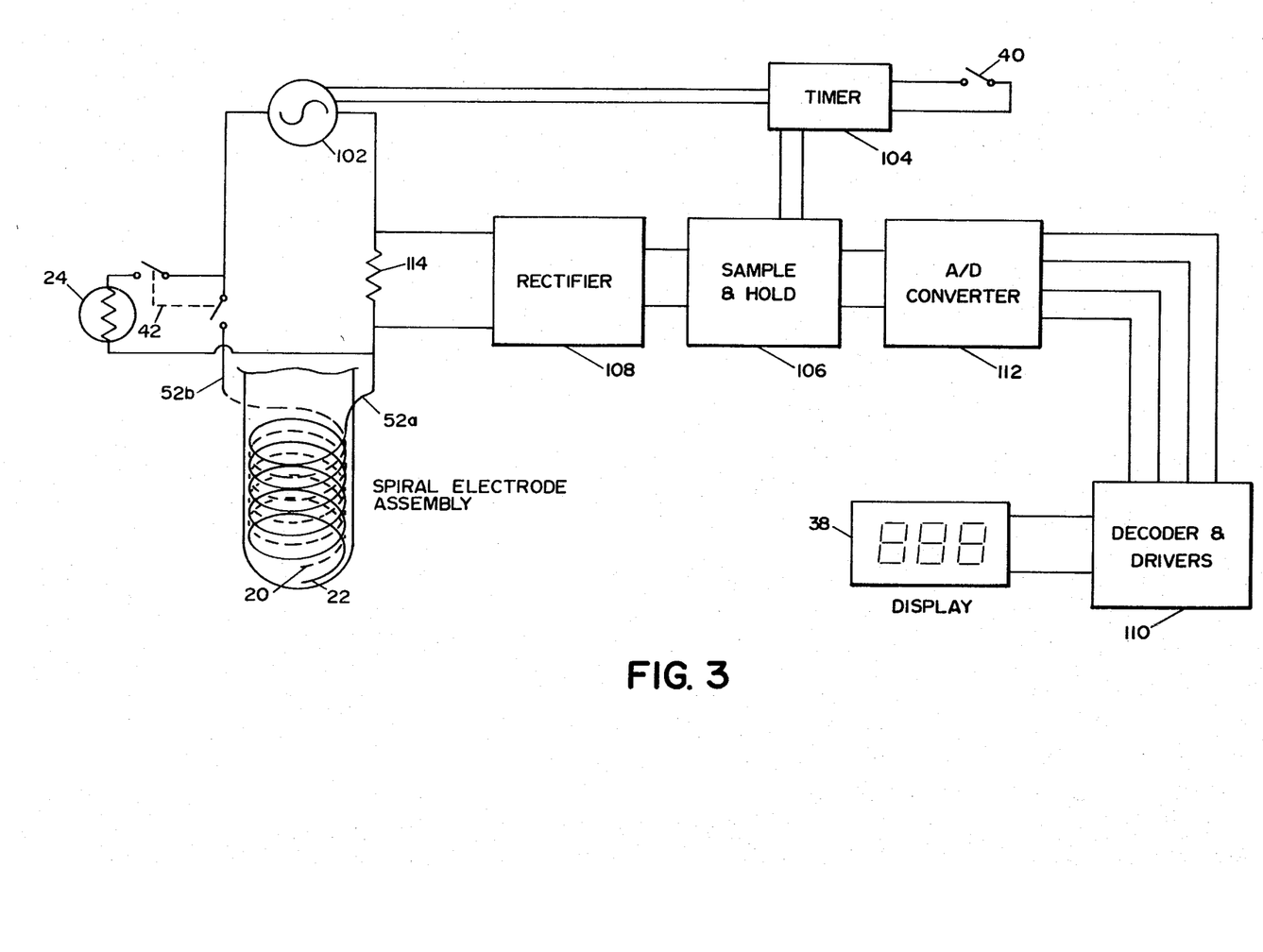
FIG. 3 illustrates an electrical diagram of the electrical circuit.

The electrical circuit 100 of FIG. 3 includes a constant current AC signal generator 102 of substantially 25 Khz. Circuitry 100 includes the generator 102, a timer 104, a sample- and-hold gate 106, and a rectifier circuit 108 between the AC generator, temperature sensor, and spiral electrodes in the sample-and-hold gate 106. In order, the LCD display 38, a decoder and drivers and buffers 110, and an A to D converter 112 connect in series to the sample-and-hold gate 106. Suitable dropping resistor 114 connects in the generator circuit. Other numerals correspond to those electrical elements previously described.

Switches 40, 42, 44, and 51 can be positioned on the back of the electronics housing 14 above the pistol-grip handle 12 for activation by an individual's thumb. The display 38 can also be mounted on the back of the housing for easy viewing in proximity to the rear portion of the fiber bundle 32 including the optic 36. A light box 64 including a light 66 connected to the power cable provides light through the coherent fiber-optic bundle 32 which secures into the light box with a grommet 68. The light is chosen to be minimal lumens output for conserving energy, yet also providing proper illumination within the vaginal cavity. Two pairs of wires 70 for the electrodes and 72 for the temperature sensor protrude from the probe, back through the elongated stainless steel rod or the like 16, into the electronics housing 14. The battery pack connects by a very flexible cable to a plug in the pistol-grip handle. A very suitable type of wire which could be utilized, since the current carrying conductor is low current, is the telephone line cord with the modular jacks in the battery pack as well as the pistol-grip cable. This provides for easy replacement of the cord as required. The switches as well as the display would be mounted on the back 74 of the electronics housing 14 as previously discussed for easy operational hand and eye movement as well as time motion. The probe, the electrodes, the length of the rod, and the particular physical placement of the components in the electronics housing can of course be suited to the particular animal or human female considerations as so required. The batteries, depending upon the circuitry which would probably be CMOS could also be incorporated into the electronics housing and handles as required, possibly elminating the need for an external battery pack. Then, the batteries would be recharged directly in the housing as so required. Other electrode configurations could be utilized, but helix electrodes are one of the preferred configurations. Any other geometricals such as spiral, circumferential or the like are also within the scope of the teachings of the invention. The electronics housing secures to the flat surface of the pistol-grip handle, but can be directly molded in to the handle as may be required.

MODE OF OPERATION

Figure 4:
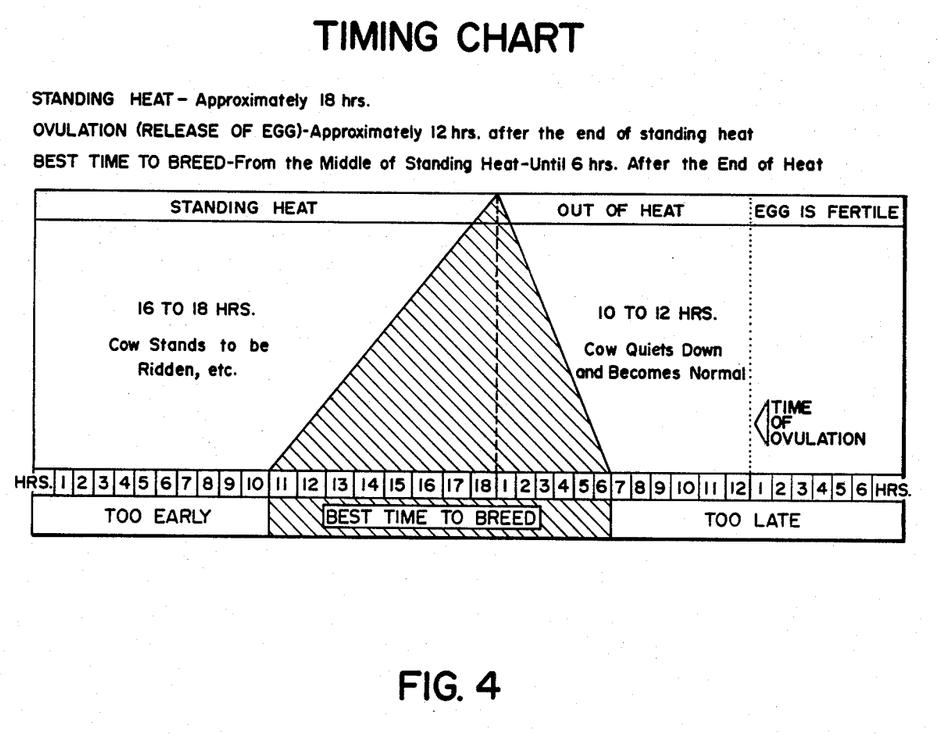
FIG. 4 illustrates an ovulation timing chart.

As the heat period in cattle is relatively short, as indicated by the graph of FIG. 4, and once a cow is observed in heat, readings are taken every twelve hours, usually in morning and evening. Without touching the external parts of the genital area of the cow with a probe 18, the probe 18 is inserted at a slightly upward angle through the vulvar lips to the urethral opening. The handle 12 is then lifted slightly and slid forward until a stable resistance indicates that the end 62 of the probe 18 has reached the cervix and the end of the vaginal tract. The color and size of the cervix are indicators of the stage of the estrus cycle and of the optimum breeding time as viewed through the eye-imaging optic 36 through the fiber-optic bundle 32 as seen by the objective lens 26. The color of the wall of the vaginal tract indicates a healthy atmosphere for sperm or indicates an infected reproductive area as an abnormality.

The electrical resistance reading of the mucus is taken by lifting the handle and looking to see through the fiber-optic lens that the probe is on the floor of the vagina to get a dorsal reading. The probe is held steady and the electrical resistance is taken for plotting of that particular animal. The animal will establish each individual set of readings, which can range on a scale from 0-1000.

During anestrus, a cow with a normal, healthy reproductive tract will have a reading of between 50 to 100. Upon the onset of estrus, the reading will fall below 50. Just prior to ovulation, the reading will fall by fifteen or more points from the normal estrus reading. Cows who show weak estrus signs or no signs at all are monitored by taking the electrical resistance reading every 24 or 36 hours. At the point where the reading falls below 50, readings are taken every twelve hours until there is another drop of 15 or more points, usually into the teens or one-digit number, indicating the preferred breeding by live cover or by artificial insemination. It must be remembered that every cow and like animal or human female is an individual and will establish her own individual readings. Breeding should be accomplished according to the pattern of readings and not specifically according to the numbers.

Figure 5:
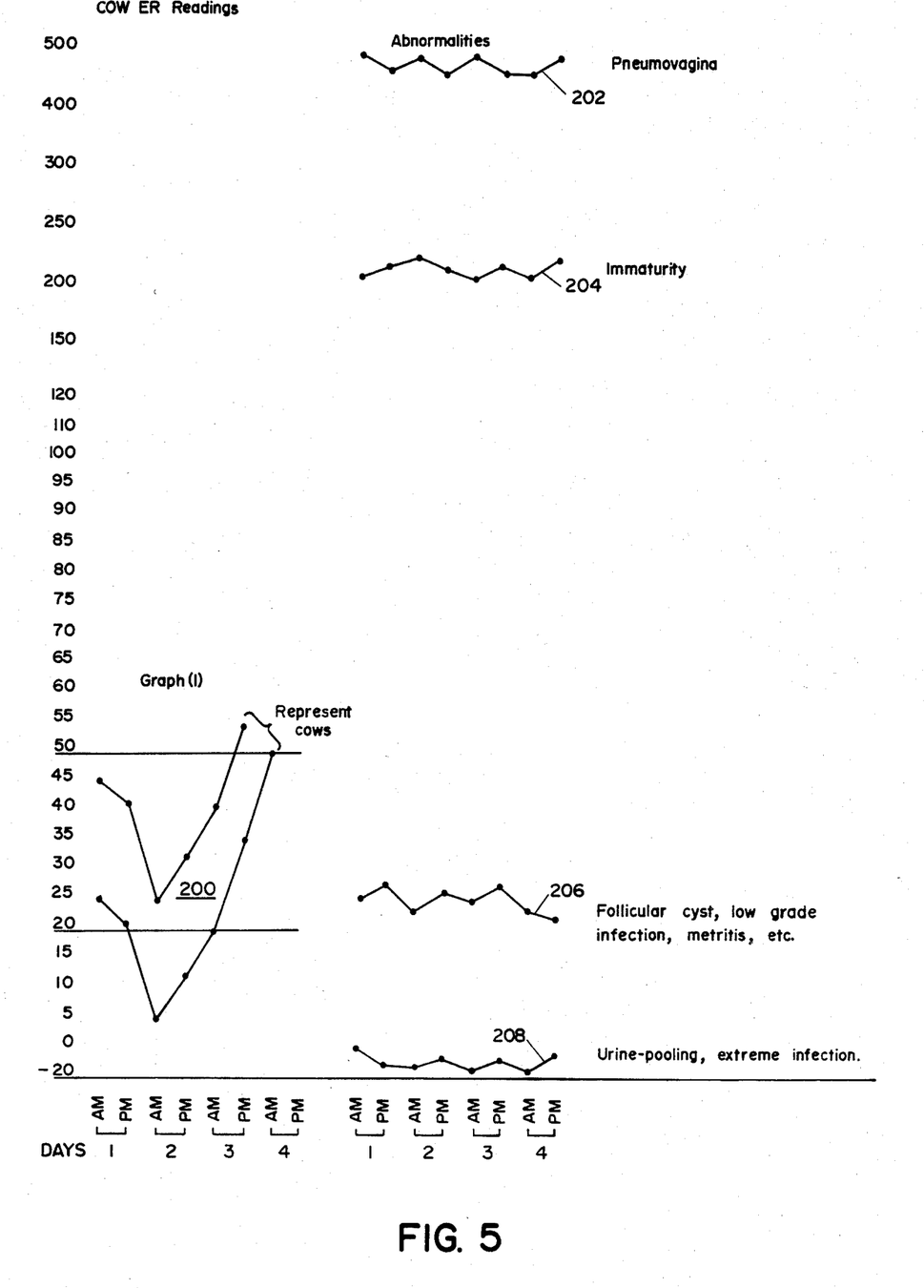
FIG. 5 illustrates electrical resistance readings for a cow.

Area 200 of FIG. 5 corresponds to the preferred range of ovulation with electrical resistance readings. The lines 202, 204, 206 and 208 represent abnormalities which occur with either very high electrical resistance readings of the mucus or very low.

Figure 6:
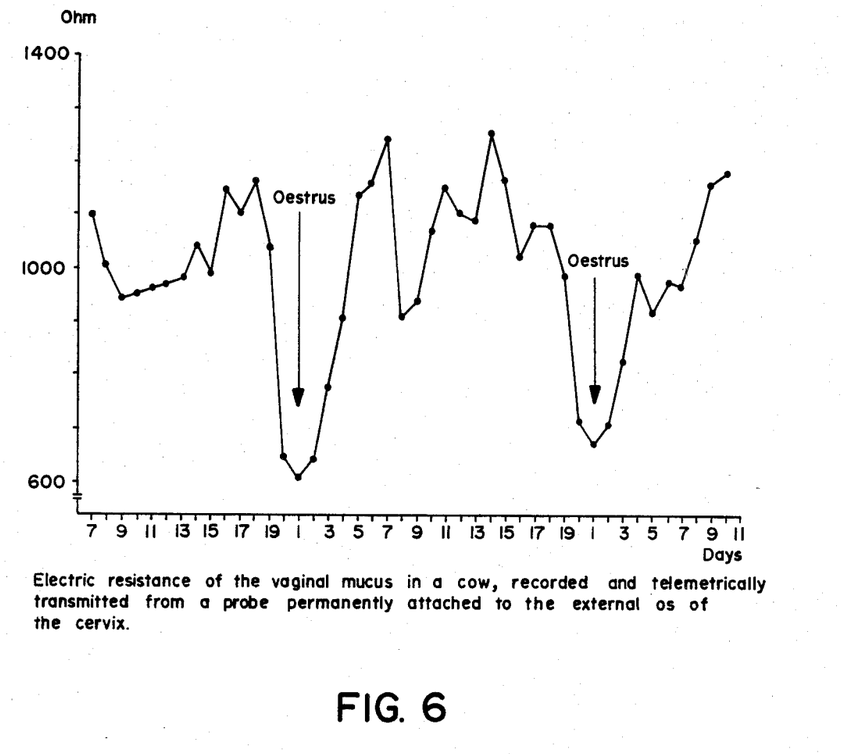
FIG. 6 illustrates electrical resistance readings of a cow plotted over a month; and, FIG. 7 illustrates electrical resistance readings for a mare.

FIG. 6 illustrates a plotted cycle in days of the electrical resistance of the mucus in a cow over the period of a month.

Figure 7:
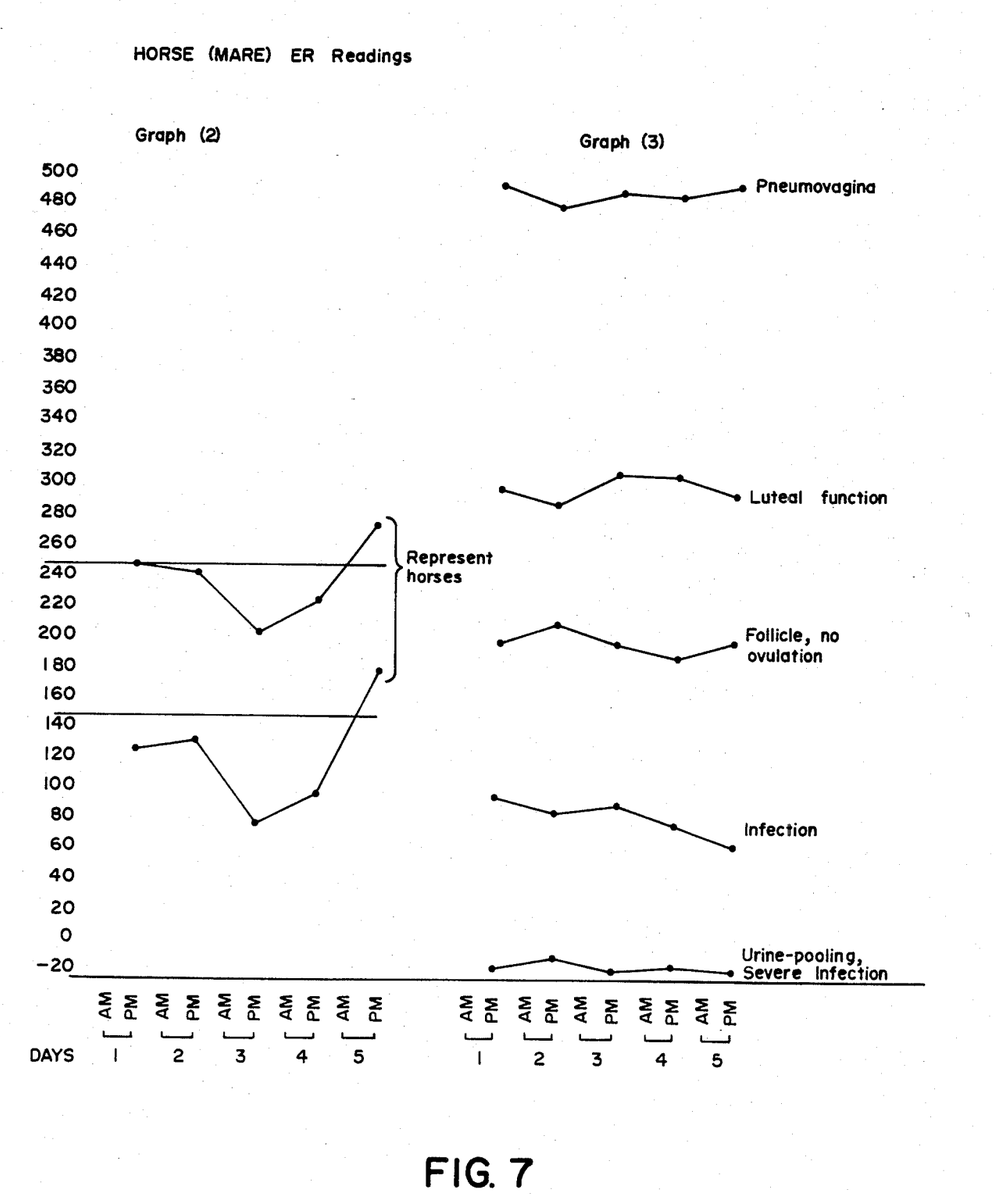

FIG. 7 illustrates an electrical resistance diagram for a horse. The diagram of FIG. 7 is similar to that of FIG. 5. If the mare is not in heat, the cervix will be small and white, protruding into the vagina with thick secretions. When the mare is in estrus, the cervix will be darker in color with stiations ranging from pale pink to red. The cervical folds and secretions will also be thinner. Immediately prior to ovulation, the cervix will be three to four times its size when not in heat. The cervix will be relaxed and lying on the bottom of the vagina with a red color and viscous fluid secretions. During pregnancy, the cervix now tight and pale will be completely sealed by thickened secretions. The fiber-optic scope will also reveal fissures or perineal lacerations. When there is a communicating passageway between the rectum and the vagina due to trauma of the previous birth, the female is rarely able to conceive. This is due to chronic contamination and infection caused by feces entering the vagina, resulting in chronic vaginitis and/or metritis. Surgical correction is often possible, therefore using the scope to monitor after birth is advised. The scope can also be used to reveal tears in the vaginal wall or the cervix, as well as detecting inflamation and abnormality exudates that indicate infection and the need for treatment. This will also be exhibited by the electrical resistance of the mucus.

As the mare's estrus cycle is longer than that of the cow, electrical resistance readings should be taken only every 24 hours, once any estrus signs have been observed. Again, each mare will exhibit her own unique set of readings. However, when not in heat, the mare will be above the 250 reading. Upon estrus, the mare will drop below 250 and 150. Upon a change from her normal estrus reading of 250 or below she will drop by 30 or more points just before ovulation. This is the optimal time for breeding. The graph shows the normal ranges of breeding for the mare as well as readings for abnormalities for mares.

Abnormalities can include metritis, follicular cysts, or other disease condition. Extremely high readings consistently abnormally high for specific species or the human female around 400-500 can indicate pneumovagina. Extremely low values, even those readings below zero, can indicate urine pooling. Urine pooling indicates that surgical correction is required.

By knowing the time of breeding, looking through the scope to observe a tight, small, pale cervix and observing high readings during the first trimester which would fall as pregnancy progresses, one can predict with a high degree of certainty the probability of pregnancy.

Readings taken at the first sign of estrus and throughout the cycle of outward heat signs showing no drop in electrical resistance readings can indicate that the female ovulated prior to showing any outward heat signs, the female ovulated post-estrus signs, the female had a follicle which did not ovulate but regressed. This frequently happens with horses early in spring or when under artificial lighting.

If on plotting the readings a "W" appears, there evidently may be twin ovulation from two follicles.

Immature females who have not begun ovulating will have a very high, abnormally high reading for that species.

The ECM system also provides for synchronization. Prostaglandin or prostaglandin analog injection in the mares with functional corpora luta induces luteolysis and estrus. Ovulatory estrus occurs within two to four days after prostaglandin treatment. Without an electrical resistance reading which shows the animal is not in heat and that the corpus luteum is present, there is no reason to give the injection of prostaglandin because it cannot function correctly. The ECM system provides the required pre-selection of animals to be treated in such a way. The cost of administering the first injection can be omitted because the system provides knowledge that the corpus luteum is present.

The use of the thermometer provides for seasonal variations with respect to environmental stresses and the reproductive cycle. Prior to ovulation, the basal temperature may be one degree Fahrenheit below the level of the preceding days but during the estrus cycle the level is somewhat higher.

Depending on use for a particular animal, the appropriate rod and probe could be selected for smaller or larger sizes of cows, horses, sheep, hogs, dogs, etc. Inherently a down-sized unit would have to be provided for use with the human female.

Various modifications can be made to the present invention without departing from the apparent scope thereof. The size of the probe and length of the rod is sized to the specifics of the individual animal. Of course for females, the instrument can be differently configured, but the specifics of operation and theory are the same.

What is claimed is:

1. Estrus cycle monitoring system for determining the preferred ovulation time of a female animal or female human, said system comprising:
   a. pistol-grip handle means having a flat upper surface;
   b. electronic housing means secured to said flat upper surface of said handle means;
   c. elongated rod secured to a forward end of said housing means, a molded rounded end probe sized for a respective animal and supporting two wound geometrically configured helix electrodes on an outer circumference of said probe, said probe including a cylindrical shape with a rounded end, said helix electrodes being longitudinally wound at an axis at an angle to said axis of said probe and rod, said probe secured to an end of said rod, wires running between said electrodes through said rod;
   d. signal processing means connected to a signal generating means connected to said electrode wires;
   e. signal display means connected to said signal processing means and positioned on a rear portion of said housing;
   f. light source means positioned in said housing means, objective lens and diffuser lens surrounding said objective lens and positioned on a rounded end of said probe, random fiber-optic bundle connected between said light source means and said diffuser lens including a covering thereabouts; coherent fiber-optic bundle extending from said objective lens, through said random fiber bundle, through said housing means, through said rear end of said housing means, and an eye-imaging optic connected to an end of said coherent fiberoptic bundle for observing the surrounding vaginal cabity and related anatomy of location of said probe; and,
   g. power means connected through a flexible cable to said housing means whereby said electrodes and electrical generating means and signal processing means display on said display means electrical resistance of mucus in a vaginal cavity of a female animal or human.

2. System of claim 1 including a temperature sensor positioned in said end of said probe, wires connecting between the temperature sensor to said signal generating and signal processing circuits.

3. System of claim 2 including a double-pull double-throw switch for switching between a temperature condition and an electrical resistance of said mucus condition displayed on said signal display means.

4. System of claim 1 including a lamp on/off switch connected between said lamp source means and said power means.

5. System of claim 1 wherein said power means is positioned in said handle means and said electronic housing means.

6. System of claim 1 wherein said signal display means comprises an LCD display for both day and night viewing.

7. System of claim 1 wherein said power means comprises a rechargeable nicad battery pack.

8. System of claim 6 including a "read" momentary push-button switch for activating the LCD display.

* * * * *